United States Patent [19]

Heine

[11] 4,012,686

[45] Mar. 15, 1977

[54] POWER SUPPLY FOR ILLUMINATED INSTRUMENT

[75] Inventor: Helmut A. Heine, Herrsching, Germany

[73] Assignees: Optotechnik, GmbH, Herrsching Upper Bavaria, Germany; Propper Manufacturing Company, Inc., Long Island City, N.Y.

[22] Filed: Mar. 18, 1971

[21] Appl. No.: 125,488

[52] U.S. Cl. ............................. 323/22 T; 128/6; 128/23; 248/205 R; 315/133; 323/39

[51] Int. Cl.² ................................. A61B 1/06

[58] Field of Search ............... 128/2.1 R, 6, 8, 9, 128/23; 315/129, 130, 133, 136; 321/18; 323/22 T, 36, 39; 340/248 C, 251, 252 R

[56] References Cited

UNITED STATES PATENTS

| | | | |
|---|---|---|---|
| 2,984,779 | 5/1961 | Klees | 323/22 T |
| 3,171,096 | 2/1965 | Murray et al. | 340/251 X |
| 3,217,232 | 11/1965 | Hamilton | 321/18 |
| 3,222,571 | 12/1965 | Timm | 315/130 |
| 3,450,130 | 6/1969 | Runge | 128/2.1 R |
| 3,539,987 | 11/1970 | Greene | 340/252 R |

*Primary Examiner*—A. D. Pellinen
*Attorney, Agent, or Firm*—Amster & Rothstein

[57] ABSTRACT

A wall mounted power supply for medical diagnostic instruments provides a continuously variable output voltage over the normal operating range of such instruments and a discreet excess voltage above the normal operating range to provide extra illumination during brief periods. The power supply output is regulated so as to be independent of load. The power supply is adapted to be conveniently wall mounted on a bracket assembly which permits quick and secure attachment and removal.

3 Claims, 8 Drawing Figures

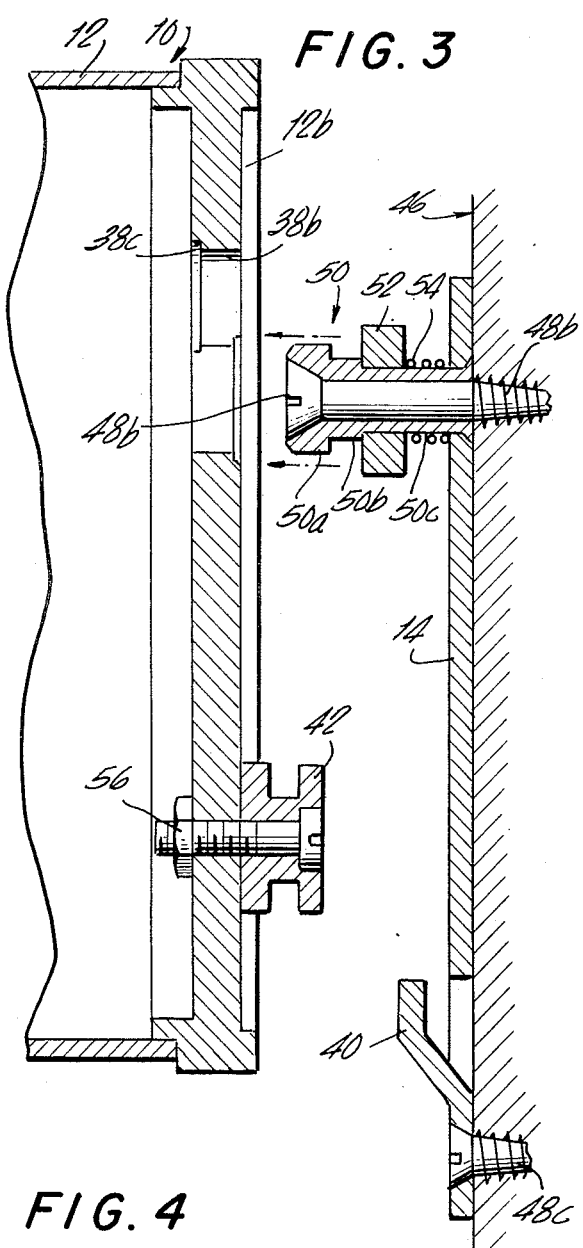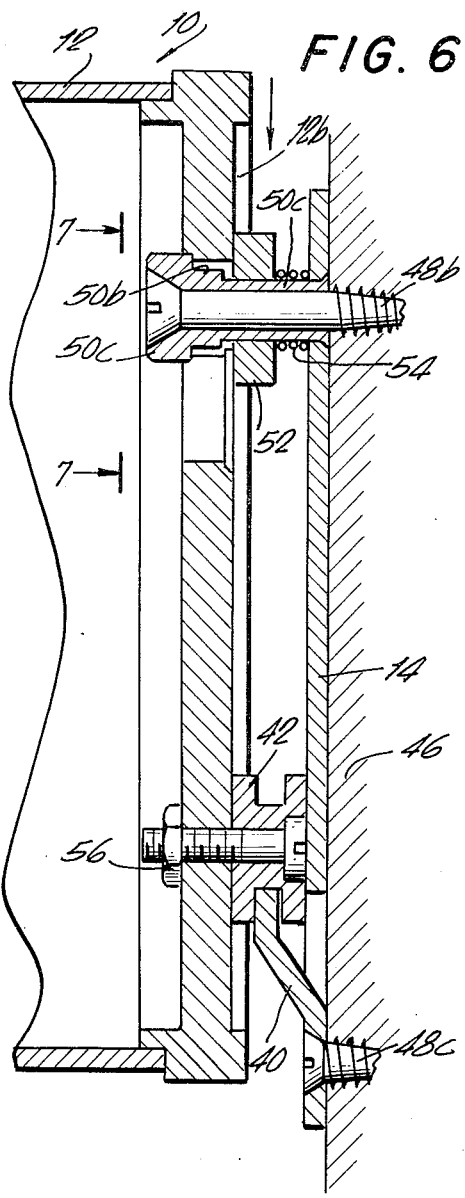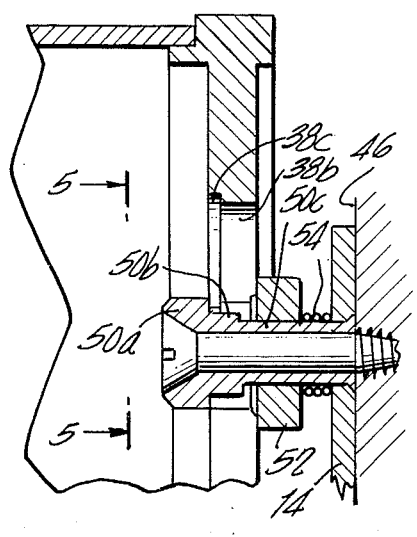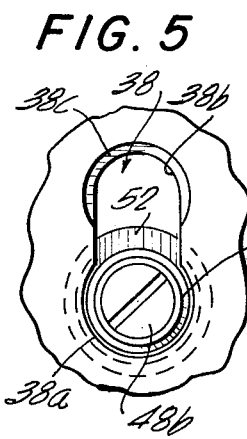

POWER SUPPLY FOR ILLUMINATED INSTRUMENT

This invention relates generally to medical diagnostic instruments and accessories therefor and more specifically to a wall mounted power supply for use primarily with illuminated diagnostic instruments.

The various illuminated endoscopic instruments (otoscopes, opthalmoscopes, etc.) used by a doctor to examine patients are conventionally battery powered by a detachable battery handle having a direct current output in the range of approximately 1 to 2.5 volts. Battery operation of such instruments is necessary when a doctor conducts examinations away from his office or hospital. However, battery operation of such instruments has several disadvantages including irregularity of illumination levels as batteries age and the need for constant replacement or recharging of batteries so that, when possible, it is desirable to use a more permanent, stable power source. The present power supply is particularly adapted for convenient use at a fixed location in a doctor's office or hospital and is adapted to power the doctor's diagnostic instruments from a normal 110 volt or 220 volt A.C. power source.

In endoscopic medical diagnostic procedures, variable illumination has been found desirable to permit the doctor to alter the contrast in the field of view to accentuate certain features of the area under observation. Applicant has also found that in some circumstances a doctor requires high intensity illumination for brief period, greater than that normally available from common low voltage lamps. Prior power supplies permit variable (though not accurately controlled) illumination over the normal instrument operating range, but make no provision for extra brightness when needed. To overcome this disadvantage, applicant's power supply is adapted to provide a continuously regulated voltage over a normal operating range of the illuminated instrument and to provide a discreet over voltage to drive the instrument beyond its normal operation range and provide extra illumination for brief periods. Applicant's power supply includes a warning light to indicate when the supply is in the over voltage condition which should not be permitted to persist for extended periods.

A further problem with fixed power supplies currently available for use with medical instruments is that their voltage output is controlled by a rheostat in the output circuit so that output voltage and hence illumination is dependent on instrument load. Applicant's power supply includes a regulating circuit, after rectification, to accurately control output voltage independent of load.

Additionally, the mounting assemblies employed in prior art wall mounted power units have made it extremely difficult to mount the power supply in the first instances and to remove it from its mounting for repair or servicing. Applicant's power supply is equiped with a unique mounting system which facilitates quick and secure mounting and removal.

It is an object of the present invention to provide a fixed power supply for use in conjunction with medical diagnostic instruments which maintains a controlled continuously variable output voltage over the normal operating range of such instruments and provides a discreet over voltage for extra illumination during brief periods.

It is a further object of the invention to provide a power supply for medical diagnostic instruments including a mounting system which permits easy and secure attachment to a wall.

In accomplishing these and other objects in accordance with the present invention, applicant's power supply includes a control circuit for regulating the DC output voltage after rectification, with the output voltage being continuously variable over a selected operating range and being adjustable to a discreet excess voltage above the selected operating range. A warning light indicates that the circuit is in its excess voltage condition.

The mounting assembly for applicant's power supply includes a mounting plate adapted to be permanently secured to a wall. The mounting plate includes a pair of mounting lugs each having a spring loaded collar adapted to be received within a keyhole slot on the rear face of the power supply chassis. A third point of support is provided by a support arm which is adapted to be received in a slotted mounting pin.

Further objects, features and advantages of the present invention will be apparent by reference to the following detailed description of a presently preferred, though nonetheless illustrative embodiment in accordance with the present invention when taken in conjunction with the appended drawings wherein:

FIG. 3 is a cross-sectional view taken along line 3—3 in FIG. 2 showing the mounting plate detached from the power supply;

FIG. 4 is a cross-sectional view similar to that of FIG. 3 showing the support lug being inserted in the keyhole slot;

FIG. 5 is a view taken along line 5—5 in FIG. 4 showing the interior of the chassis;

FIG. 6 is a cross-sectional view similar to that of FIG. 3, showing the power supply in its mounted position;

FIG. 7 is an interior view taken along line 7—7 in FIG. 6; and

Figure 1:
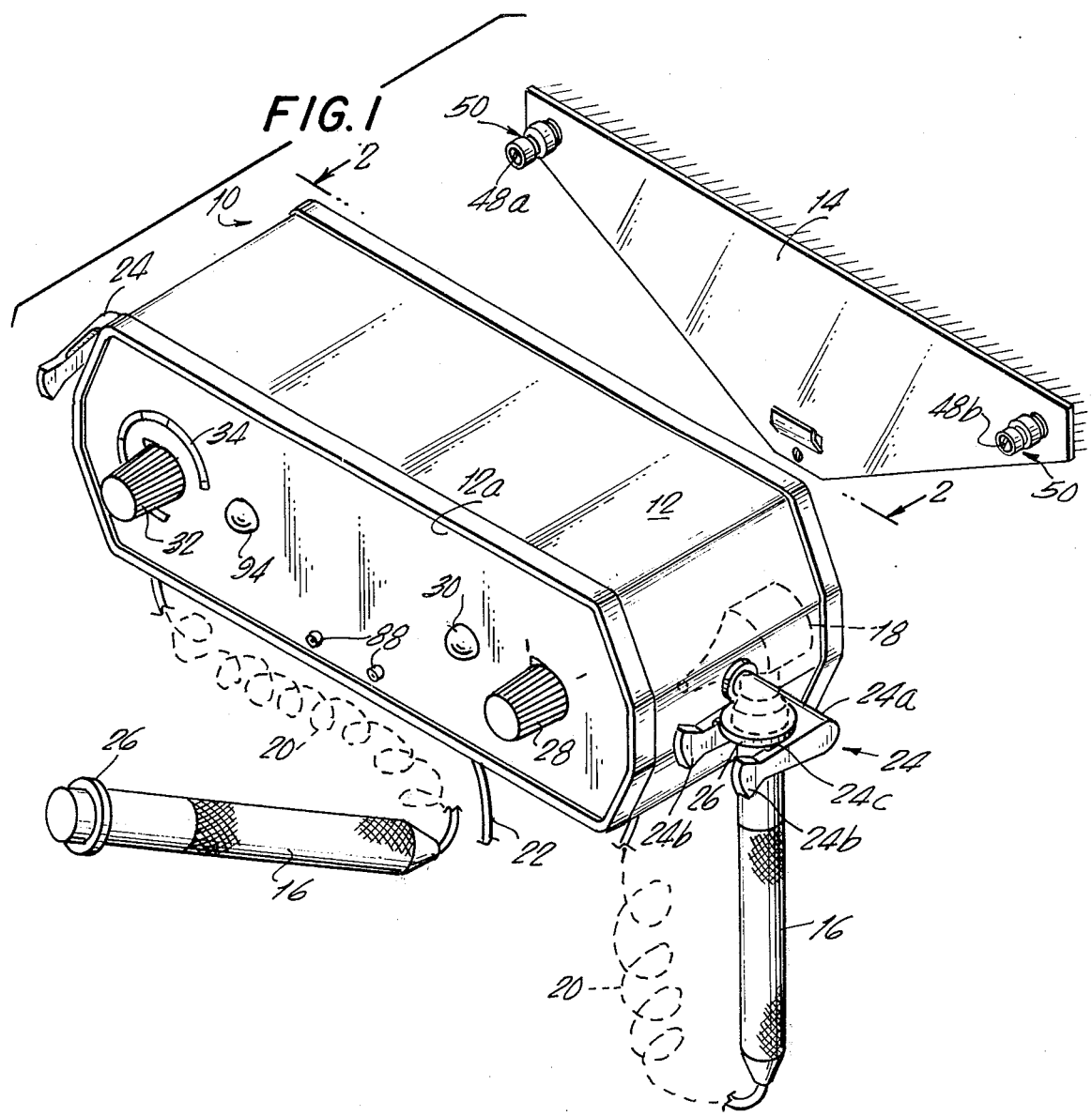
FIG. 1 is a perspective view of the power supply with the mounting plate detached.

The wall mounted power supply generally designated 10 in FIG. 1 includes as its basic components a power supply chassis 12 adapted for mounting on a mounting plate 14 which is designed to be permanently affixed to a wall in a doctor's office, hospital or other regular examining location. The power supply includes a pair of instrument handles 16 adapted to receive conventional medical diagnostic instruments such as the otoscope head 18 shown in broken line in FIG. 1. The instrument handles are connected by coil power cords 20 to the power supply chassis 12. An AC power line 22 is provided to interconnect the power supply with a source of conventional AC line current of either 110 or 220 volts. When not in use, instrument handles 16 and instrument 18 are adapted to be supported in instrument cradles 24 which extend from the sides of chassis 12. Cradles 24 include a shaft portion 24a and a pair of forward extending arms 24b having a depressed seat 24c designed to receive an annular collar 26 on the instrument handles 16. The shaft portion 24a of the cradle is connected to a microswitch (not shown) within chassis 12 adapted to turn the power in cords 20 off when handle 16 is lodged in cradle 24. Cradle 24 is spring loaded so that when the instrument handle is removed for use, the microswitch is closed, applying power to handle 16.

The basic power supply controls are located on the face 12a of the chassis 12 and include a rotary on-off switch 28, an indicator light 30 which is illuminated when AC power is applied to the power supply circuit, and a rotary voltage control switch 32 with a pointer. Face 12a includes a scale 34 which is marked continuously over first voltage range (for example between 1 and 2.5 volts) and includes a discreet setting at a fixed over voltage position (for example 3 volts). Switch 32 is adapted so that it may be adjusted continuously over the 1 to 2.5 voltage range and switches from the continuous range to a discreet over voltage position when turned fully clockwise. As will be explained in more detail in connection with the schematic showing of FIG. 8, lamp 30 is provided to be illuminated whenever switch 32 is in its over voltage position, thereby warning the user of the over voltage condition which should not be permitted to persist for long periods of time.

Figure 2:
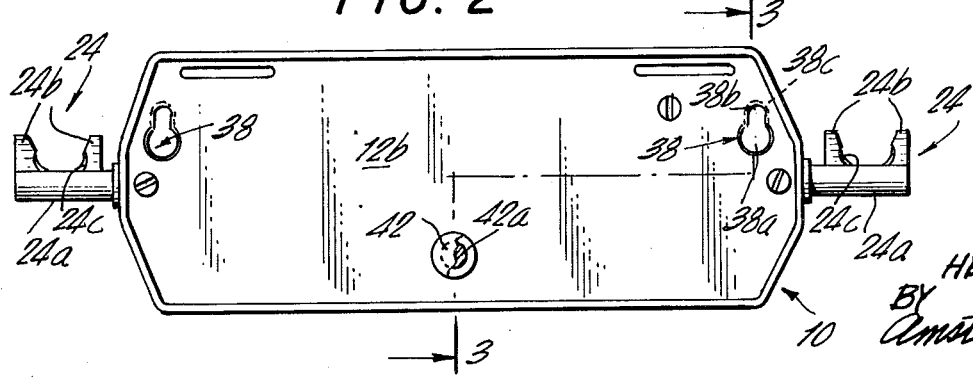
FIG. 2 is a rear view of the power supply without the mounting plate.

FIG. 2 shows the rear face plate 12b of chassis 12 with instrument handles 16 removed. Note that the forward extending arms 24b of cradles 24 are in a slightly raised position by virtue of the spring described above.

Mounting plate 14 is adapted to support chassis 12 by means of retaining lugs 50 which engage keyhole slots 38 (in FIG. 2) and by support arm 40 which engages slotted pin 42 as described in more detail in connection with FIGS. 3-7.

Referring to FIG. 3, wall mounting bracket 14 is permanently secured to wall 46 by screws 48 a, b and c. Screws 48 a and b are positioned through the center of the hollow support lug 50 so as to provide the most rigid contact with wall 46 at the point of highest strain.

Each of support lugs 50 includes a broad head section 50a, a narrower neck section 50b and a still narrower body section 50c. Each lug is fitted with an annular collar 52 which is adapted to fit over and slide freely upon body section 50c and to be stopped against the inner lip of neck section 50b. Each lug includes a coiled spring 54 positioned between plate 14 and the annular collar 52 to maintain the collar 52 tensed against neck section 50b.

The keyhole slots 38 in the rear plate of the power supply chassis each include a large open section 38a and a narrow slotted section 38b. The interior face of back plate 12b includes a circular routed out section 38c about the slot 38b. Section 38c is adapted to receive the circular head 50a of pin 50.

Back plate 12b also includes slotted pin 42 secured to the back plate by a nut and bolt 56. Pin 42 includes an annular channel 42a around its circumference dimensioned to receive arm 40 which extends forwardly and upwardly from the mounting plate 14.

To mount the power supply, plate 14 is screwed or otherwise affixed to the wall. The power supply rear plate 12b is forced back onto support lugs 50 with the rear face of plate 12b forcing collar 52 towards plate 14 (against the action of spring 54). At the same time, arm 40 is lined up with slot 42a in pin 42.

FIG. 4 shows the support lug received within the keyhole slot with spring 54 compressed.

The chassis is then lowered downwardly onto the mounting plate so that the broad head 50a of pin 50 becomes seated in cavity 38c (FIG. 6). At the same time, the upper edge of support arm 40 enters in annular channel 42a. This arrangement provides a sturdy 3 point support for the power supply. At the same time, the power supply is prevented from jarring loose by virtue of the engagement of head 50a in seat 38c.

To remove the unit, the entire power supply is forced rearwardly compressing spring 54 and raising head 50a away from the interior face of rear plate 12b. The unit is then raised withdrawing support arm 40 from slot 42a and bringing lugs 50 in alignment with the broad open sections 38a of the keyhole slots. The wall unit may then be conveniently removed from the mounting plate.

Figure 8:
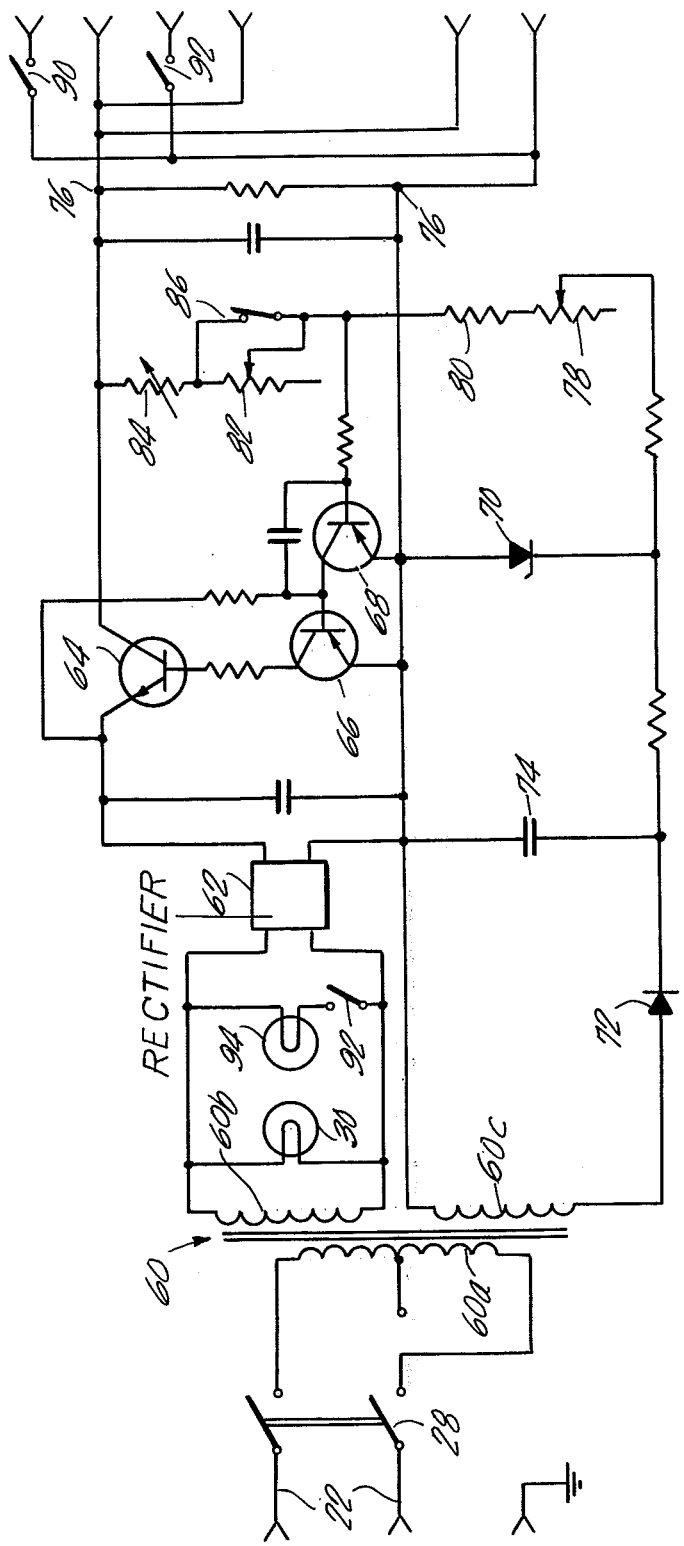
FIG. 8 is a schematic diagram of the circuit of applicant's power supply.

Referring to the schematic drawing of FIG. 8, it will be seen that applicant's power supply is adapted to operate from conventional AC mains on power cord 22. AC power is bi-polar switched by switch 28. Bi-polar switching eliminates any possibility of shock injury to the doctor or the patient. The AC line is connected across the primary winding of transformer 60 with a center tap on the primary winding so that the instrument may be adapted for 110 or 220 volt use.

The secondary winding 60b is adapted to deliver an AC voltage across indicator lamp 30 which is thus illuminated whenever AC power is applied to the power supply. Secondary winding 60c provides an auxiliary voltage for the control circuit.

The output of secondary 60b is rectified in rectifier 62 and the DC output of rectifier 62 is regulated by a control circuit including transistor 64 as a series resistance with transistors 66 and 68 operating as control voltage amplifiers. The emitter of transistor 68 is maintained at a constant voltage by zener diode 70 which is powered from secondary winding 60c through a rectifier circuit consisting of diode 72 and capacitor 74. The output voltage across output terminals 76 is determined by the voltage divider including adjustable resistor 78, resistor 80, adjustable resistor 82 and variable resistor 84. By adjusting variable resistor 84 through control knob 32 on the control panel face (with switch 86 open) the output voltage across output terminals 76 is regulated. The resistors are selected such that the output across terminals 76 may be continuously varied from approximately 1 to 2.5 volts, the normal operating range of the instruments for which the power supply is adapted. It will be seen that output terminals 76 include three branches having three separate pairs of output leads, two pairs going to handle 16 and a third pair going to auxiliary output 88 on face plate 12a to power instruments not adapted to be received in handles 16. The output circuits going to handles each include a microswitch 90, 92 which is controlled by the pivotal motion of the instrument handle cradles 24 in the manner previously described.

In operation, the output voltage across the output terminals is controlled by varying the resistance of variable resistor 84 in the range from approximately 1 to 2.5 volts. To reach the over voltage condition, switch 86 is opened adding resistance 82 to the upper side of the voltage divider. Switch 86 is controlled by rotary dial 32 and is opened when 32 is turned to its full clockwise position. The shaft of switch 32 also includes switch 92 which closes the AC power circuit from secondary winding 60b across bulb 94 when switch 86 is opened, giving a visual indication that the power supply is in its over voltage condition. Since the three volt output applied to a conventional lamp for diagnostic instruments will burn the bulb out rapidly, the over voltage condition should not be used for extended periods. However, it may be used sufficiently long to permit the brief periods of high illumination required by the doctor.

The above described embodiments are merely examples of the present invention as defined in the following claims. Numerous other embodiments will be apparent to those skilled in the art without departing from the spirit or scope of the invention.

What is claimed is:

1. A power supply for illuminated medical diagnostic instruments comprising input terminals adapted to be connected to a source of alternating current, a rectifier communicating with said input terminals for rectifying said alternating current, output terminals adapted to be interconnected with one or more illuminated medical diagnostic instruments, and a control circuit communicating with said rectifier and said output terminals for variably regulating the voltage at said output terminals over a continuous normal operating range corresponding substantially to the normal operating range of the illuminating device of said instruments and for providing a discrete output voltage above said normal operating range to give extra illumination for brief periods.

2. A power supply in accordance with claim 1 further including an indicator lamp adapted to be illuminated when the voltage at said output terminals is said discreet excess voltage.

3. A power supply in accordance with claim 2 including one or more cradles for receiving said diagnostic instruments, each said cradle including switch means for breaking the circuit to said instrument when it is positioned in said cradle.

* * * * *